(12) United States Patent
Fadler

(10) Patent No.: US 7,086,779 B2
(45) Date of Patent: Aug. 8, 2006

(54) MEDICAL X-RAY DIAGNOSTIC INSTALLATION HAVING TWO X-RAY RADIATORS THAT SELECTIVELY INTERACT WITH A SIGNAL RADIATION DETECTOR

(75) Inventor: Franz Fadler, Hetzles (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/652,271

(22) Filed: Aug. 29, 2003

(65) Prior Publication Data

US 2004/0066907 A1 Apr. 8, 2004

(30) Foreign Application Priority Data

Sep. 5, 2002 (DE) ................................ 102 41 189

(51) Int. Cl.
*H05G 1/02* (2006.01)
(52) U.S. Cl. .......................... 378/196; 378/198; 378/4; 378/21
(58) Field of Classification Search ................. 378/193, 378/195–198, 115, 116, 4–27
See application file for complete search history.

(56) References Cited

U.S. PATENT DOCUMENTS

| 4,349,740 A | | 9/1982 | Grassmann et al. ........... 378/25 |
| 5,067,145 A | * | 11/1991 | Siczek et al. ................ 378/198 |
| 5,416,824 A | | 5/1995 | Goldhorn et al. ........... 378/189 |
| 5,523,554 A | | 6/1996 | Hassler et al. ............ 250/208.1 |
| 6,155,713 A | * | 12/2000 | Watanabe .................... 378/197 |
| 6,264,364 B1 | | 7/2001 | Pflaum et al. .............. 378/196 |
| 6,325,537 B1 | * | 12/2001 | Watanabe .................... 378/197 |
| 6,359,966 B1 | | 3/2002 | Schulz ....................... 378/98.3 |
| 6,742,929 B1 | * | 6/2004 | Horbaschek ................ 378/197 |
| 6,888,919 B1 | * | 5/2005 | Graf ............................ 378/65 |

FOREIGN PATENT DOCUMENTS

EP 0 877 538 11/1998

OTHER PUBLICATIONS

"Radiologische Technik in Röntgendiagnostik Und Strahlentherapie," Köcher (1982) pp. 118-121.
"Digitale Detektorsysteme für die Projektionsradiographie," Schulz, Fortschritte auf dem Gebiet der Röntgenstrahlen und der Bildgebenden Verfahren (Röfo), vol. 173 (2001) pp. 1137-1146.

* cited by examiner

*Primary Examiner*—Edward J. Glick
*Assistant Examiner*—Jurie Yun
(74) *Attorney, Agent, or Firm*—Schiff Hardin LLP

(57) ABSTRACT

A medical X-ray diagnostic installation has a first X-ray radiator attached to a C-arm as well as a second X-ray radiator that is mounted separately from the C-arm at a holder device that can be attached to a stationary structure. A radiation receiver that optionally detects the X-rays emitted by the first X-ray radiator or the X-rays emitted by the second X-ray radiator is attached to the C-arm. The radiation receiver can preferably be rotated around an axis that resides perpendicularly on the plane defined by the C-arm. With this X-ray diagnostic installation, standard examinations for conventional C-arm devices can be implemented and tomographic exposures can be generated upon employment of the second X-radiator.

13 Claims, 2 Drawing Sheets

MEDICAL X-RAY DIAGNOSTIC INSTALLATION HAVING TWO X-RAY RADIATORS THAT SELECTIVELY INTERACT WITH A SIGNAL RADIATION DETECTOR

BACKGROUND OF THE INVENTION

1. Field of the Invention

The present invention is directed to a medical X-ray diagnostic installation of the type having a C-arm, an X-ray radiator attached to the C-arm, and a radiation receiver also attached to the C-arm for detecting X-rays emitted by the X-ray radiator.

2. Description of the Prior Art

German Patent 43 16 130 discloses an X-ray diagnostic installation with an image intensifier that can be horizontally aligned in a standby position or situated outside the region of the patient support plate. This achieves a lower height of the support plate and thus makes it easier for a patient to get on it.

A medical X-ray diagnostic installation of the type initially described is disclosed, for example, by German OS 198 39 620 or European Application 0 877 538. A number of different examinations at the patient is possible with such conventional C-arm devices.

However, it is not possible with known C-arm devices to implement tomographic methods as described, for example, in the book by Köcher, Radiologische Technik in Röntgendiagnostic und Strahlentherapie, VEB Verlag Volk und Gesundheit, Berlin, 1982, pages 118 through 121, or DE 26 58 533 C2. In the fluoroscopy direction, it is only possible to sharply image one specific slice of the transirradiated subject in a specific, so-called slice height or slice level. The regions lying in front of or behind this slice plane are smeared to such an extent due to artificially generated motion unsharpness that they are not imaged. This is therefore also referred to as a "smearing technique".

SUMMARY OF THE INVENTION

An object of the present invention is to provide a medical X-ray diagnostic installation with which examinations of the type conventionally undertaken will C-arm devices, as well as tomographic exposures can be implemented.

In a medical X-ray diagnostic installation of the type initially described, this object is inventively achieved by a holder device for holding a second X-radiator that is attachable to a stationary structure separately from the C-arm, and the radiation receiver optionally detects the X-rays emitted by the C-arm-mounted X-ray radiator or the X-rays emitted by the second X-ray radiator.

With the medical X-ray diagnostic installation of the invention, a tomographic exposure can be implemented by the interaction of the second X-ray radiator with the radiation receiver. To this end, at least two of the second X-ray radiator, the examination subject, and the radiation receiver must be moved relative to one another. Compared to two mutually independent X-ray devices of which one is a C-arm device and the other is an examination device suitable for tomographic exposures, the X-ray diagnostic installation of the invention has the advantage that only a single radiation receiver is needed. This facilitates the operation and also lowers the acquisition costs. The allocation of one of the two X-ray radiators to the radiation receiver can be manually undertaken by operating personnel or automatically by a control device dependent on the selected examination program.

As already mentioned, examinations that are specific to the C-arm as well as tomograms are possible with the X-ray diagnostic installation of the invention, to which end a drive device in the X-ray diagnostic installation is preferably fashioned for the latter type of examinations. For example, the relative motion sequences between the second X-ray radiator and the radiation receiver to be implemented for a smear technique can be stored in the drive device, so that these can be called by a corresponding selection entry and can be executed by the on drive provided therefor.

Independently thereof, the medical X-ray diagnostic installation of the invention also has the advantage that the second X-ray radiator in interaction with the radiation receiver can be fashioned as a replacement for a conventional raster wall apparatus.

The stationary structure to which the holder device for the second X-ray radiator is attachable is preferably a ceiling of the examination room.

In a preferred embodiment, the radiation receiver is pivotably seated such that it can be aligned both with respect to the first X-ray radiator mounted to the C-arm as well as with respect to the second X-ray radiator.

Proceeding from a status wherein the radiation receiver is directed toward the first X-ray radiator, for example, the C-arm with the first X-ray radiator is slightly orbitally moved. The second X-ray radiator can now be positioned at the location that thereby becomes free and that was previously occupied by the first X-ray radiator. In order to achieve an allocation of the second X-radiator to the radiation detector, which was also orbitally moved, the latter must still be moved in a direction toward the second X-ray radiator as a final step.

As a result of the pivoting movement of the radiation receiver, the central ray of the detectable ray bundle migrates slightly in the examination subject or patient. It is therefore for the patient support mechanism to be adjustable transversely relative to the patient axis, so that a corresponding position-correction of the patient can be implemented dependent of the pivoting.

The radiation receiver preferably is rotated around a rotational axis that is perpendicular to the plane defined by the X-arm. In particular, the radiation receiver is isocentrically suspended, particularly such that the respective central rays of the two X-rays radiators intersect in the rotational axis.

In order to be able to implement a smear technique in a simple way, it is expedient for the radiation receiver and the second X-ray radiator to be movable relative to one another parallel to the patient axis, particularly oppositely directed.

The relative motion can be realized, for example by the C-arm with the radiation receiver attached thereto being movable along a first guide parallel to the patient axis and/or by the second X-radiator being movable along a second guide—for example, in the opposite direction—parallel to the patient axis.

The radiation receiver is fashioned, for example, as an image intensifier system, or as a conventional film/foil system.

In a preferred embodiment, however, the radiation receiver is fashioned as a flat image detector, particularly as a solid-state matrix detector system. Such a flat image detector, which yields considerable advantages as to the image processing and management, however, is rather expensive. In conjunction with such a flat image detector, it is therefore especially advantageous to unite two different functionalities in an X-ray diagnostic installation with only a single detector.

In another preferred embodiment, the holder device for the second X-ray radiator is a mount that is extensible in the vertical direction in telescoping fashion and having a free end to which the second X-ray radiator is attached.

The second X-ray radiator preferably is attached to the holder device so as to be rotatable around a horizontal rotational axis that proceeds perpendicular to the patient axis. Given a relative motion between the second X-ray radiator and the radiation receiver for the acquisition of a longitudinal body slice, the drive device of the X-ray diagnostic installation can set the rotational angle of the second X-ray radiator with respect to the rotational axis so that in every longitudinal position the second X-radiator is always directed toward the radiation receiver. To this end, it is also advantageous for the radiation receiver also to be tiltable around a tilting axis that proceeds parallel to the plane of the C-arm in addition to the degree of freedom of motion with respect to the rotational axis. A tiltability of the radiation receiver during the implementation of a motion sequence in the smear technique is not absolutely necessary. Work can also be carried out with a radiation receiver or image intensifier that is not angularly readjusted.

Especially advantageously, moreover, the second X-ray radiator can be rotated into a position wherein an X-ray bundle can be emitted in the horizontal direction, and the radiation receiver can be turned toward the second X-radiator in this position. As a result, an X-ray exposure can be implemented in a simple way at, for example, a standing patient, and the X-ray diagnostic installation can be operated in the mode of a raster wall device.

DESCRIPTION OF THE PREFERRED EMBODIMENTS

Figure 1:
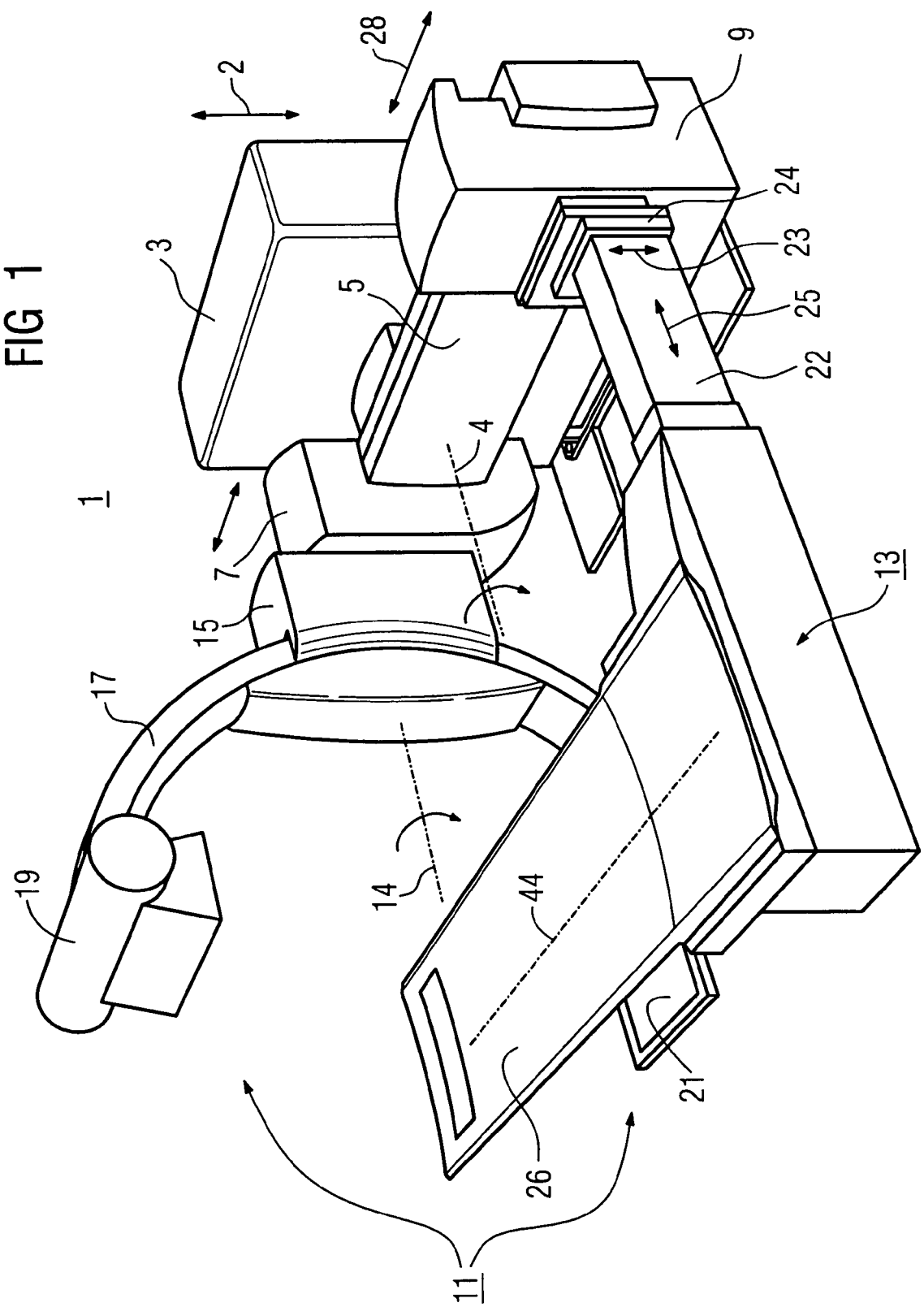
FIG. 1 shows an example of an X-ray examination apparatus on which the invention is based, in a perspective view.

FIG. 1 shows an X-ray examination apparatus 1 that stands on the floor of an examination room via a base 3 that is height-adjustable along the arrow 2. A guide rail 5 that is rotatable by ±90° around a horizontal axis 4, relative to the illustrated horizontal position is seated at the base 3. A clamp-like, first carriage 7n and a clamp-like, second carriage 9 are movably secured on the guide rail 5.

The first carriage 7 carries an X-ray exposure system referenced 11 overall, and the second carriage 9 carries a patient support mechanism referenced 13 overall.

The X-ray exposure system 11 has a guide element 15 that is seated at the first carriage 7 so that the guide element 15 is rotatable around a horizontal axis 14. The guide element 15 forms a circularly curved guide for the acceptance of a C-arm 17 at the side facing away from the carriage 7. The C-arm 17 can execute a circular arc-shaped or orbital movement in the guide element 15, so that a vertical as well as a horizontal transirradiation of the patient is possible. In the illustrated example, the C-arm 17 carries an X-ray radiator 19 at its upper end and an X-ray detector 21 at its lower end, particularly a flat detector or some other digital image receiver or an X-ray image intensifier system, for example fashioned with a luminescent screen, amplifying electron optics, optional light optics and video or CCD camera. Such a system is described, for example, in the article by R. F. Schulz, "Digitale Detektorsysteme für die Projecktionsradiographie," in Fortschritte auf dem Gebiet der Röntgenstrahlen und der bildgebenden Verfahren (Röfo), Volume 173, 2001, pages 1137 through 1146.

The specifically illustrated fashioning of the detector 21 as a flat image detector or flat detector is realized, for example, as a solid-state detector with a scintillator layer, for example with cesium iodide (CsJ), gadolinium oxide sulfide (GOS) or amorphous selenium, with allocated CCD elements or photodiodes, for example on a basis of hydrogenated amorphous silicon (a-Si:H), as well as with a corresponding readout electronics. Such an a-Si detector is likewise described in the article by R. F. Schulz as well as in German Patent 43 21 789 (see page 2, lines 41 through 65) and German OS 100 15 264 (see column 1, line 37 through column 2, line 48), which are incorporated herein by reference. A flat image detector has a number of detector elements (not explicitly shown here) arranged in a matrix in a detector plane in, for example, orthogonal detector columns and rows, the detector elements having a typical pixel size of 100 μm. The active sensitive area has a size of, for example, 40 cm×40 cm.

The patient support mechanism 13 has a cantilevered arm 22 that is secured to a base 24 that is seated at the second carriage 9 adjustable in height in the arrow direction 23. Toward one side, a support plate 26 for the patient is attached to the end of the arm 22 that can be extended telescopically in the arrow direction 25. The telescoping extension of the arm 22 produces a transverse lift of the support plate 26, and the displaceability of the second carriage 9 along the guide rail 5 (arrow direction 28) produces a longitudinal adjustment.

Figure 2:
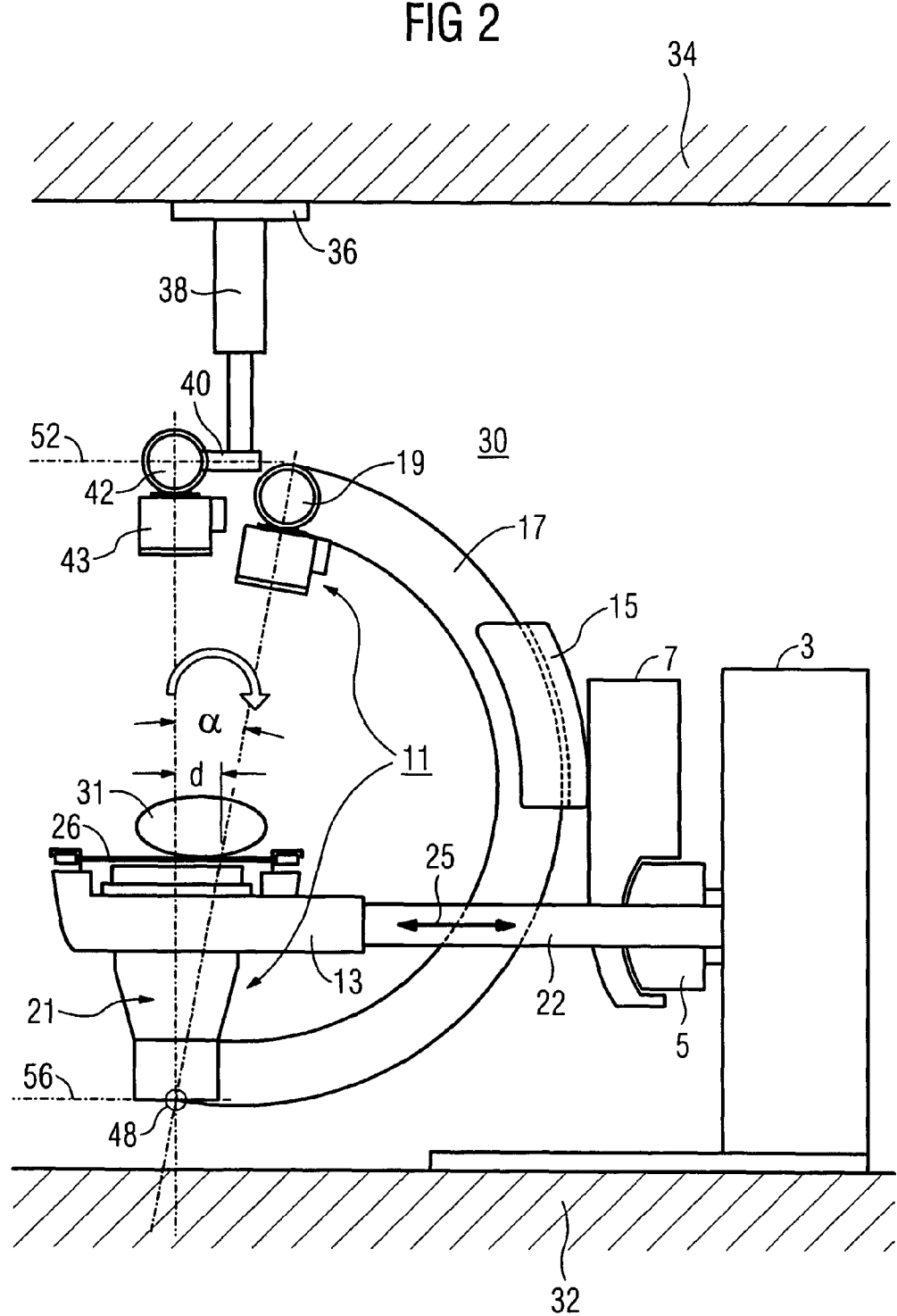
FIG. 2 shows an X-ray diagnostic installation of the invention in a side view.

FIG. 2 shows an X-ray diagnostic installation 30 of the invention that essentially corresponds to the X-ray examination apparatus 1 of FIG. 1 with respect to the components connected to the C-arm 17 and the patient support mechanism 13.

In contrast to the X-ray examination apparatus 1 specifically illustrated in FIG. 1, the X-ray diagnostic installation 30 of FIG. 2 has a radiation receiver 21 fashioned as an X-ray image intensifier system, whereas a flat image detector is shown as an example in FIG. 1. According to FIG. 2, moreover, no second carriage 9 is present at the guide rail 5 functioning a first guide. On the contrary, the arm 22 with the patient support mechanism 13 is rigidly secured to the base 3. The difference in view of this fastening as well as the difference in view of the configuration of the radiation receiver 20 are not limiting for the X-ray diagnostic installation 30 of the invention. On the contrary, both configurations are possible according to the invention. A patient under examination is indicated with reference character 31.

As in FIG. 1, the components pf the X-ray diagnostic installation 30 according to FIG. 2 that belong to the C-arm 17 are seated in secure fashion on a floor 32 of an examination room via the base 3. A vertical mount 38 that can be downwardly extended in telescoping fashion is attached to a ceiling 34 of the same examination room via a ceiling rail 36 serving as second guide. A second X-ray radiator 42 together with diaphragm device 43 is secured to the lower end of the mount 38 via a small arm 40. The ceiling rail 36 extends perpendicularly to the plane of the drawing, i.e. parallel to the patient axis 44 (see FIG. 1), so that the second X-ray radiator 42 is linearly adjustable in this direction.

In the illustrated status, the radiation receiver 21 and the second X-ray radiator 42 are aligned to one another. In this status, tomographic exposures can be implemented with the X-ray diagnostic installation 30 of the invention. To this end, the second X-ray radiator 42 and the radiation receiver 21 execute a coupled, oppositely directed motion perpendicular to the plane of the drawing, i.e. parallel to the patient axis 44. The slice height as well as the slice thickness can be defined by the setting of the motion parameters. The above-cited book by Köcher, Kriester, pages 118 through 122, is referenced for details with respect thereto, and is incorporated herein by reference.

When, proceeding from the condition shown in FIG. 2, a conventional C-arm examination (with vertical transirradiation) is to be implemented with the X-ray diagnostic installation 30 of the invention, then the second X-radiator 42 is displaced by a movement along the ceiling rail 36, so that the first X-radiator 19 is positioned roughly in this position by an azimuthal (orbital) movement of the C-arm 17 in the guide element 15. The first X-ray radiator 19, for example, can then radiate perpendicularly downwardly. In order to now align the radiation receiver 21 to the first X-ray radiator 19, this is rotated by an angle α around a rotational axis 48 that proceeds parallel to the patient axis 44. The rotation by the angle α is necessary since not only the first X-ray radiator 19 but also the radiation receiver 21 are differently oriented in space in the azimuthal or orbital movement of the C-arm 17, since the two are connected to one another via the C-arm 17.

The rotation of the radiation receiver 21 is isocentric such that the central rays of the X-ray bundles respectively emitted by the two X-ray radiators 19, 42 intersect in the axis 48. The rotation around the axis 48 can be implemented either manually or motorized. As a result of the rotational motion around the axis 48, it is advantageous for a continued examination of the examination subject 31 to move the examination subject 31 is in the direction of the double arrow 25 toward the base 3, by a length d of transverse table motion so that the examination subject is likewise transirradiated centrally or at the same location in this second examination mode wherein the C-arm 17 is utilized.

When the second X-ray radiator 42 is rotated by 90° and the C-arm 17 with the radiation receiver 21 is also rotated by 90° around the horizontal axis, then given horizontal transirradiation—exposures at standing patients are possible as in the case of a raster wall device.

An X-ray diagnostic installation thus is provided that has expanded functionality compared to the conventional equipment.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical X-ray diagnostic installation comprising:
   a C-arm examination apparatus, including a C-arm;
   a first X-ray radiator attached to the C-arm;
   a radiation receiver attached to the C-arm for detecting X-rays emitted by the first X-ray radiator;
   a patient support having a surface adapted to receive a patient thereon, said patient support being disposed between said first x-ray radiator and said radiation receiver;
   a second X-ray radiator; and
   a mount to which said second X-ray radiator is attached to position said second x-ray radiator at a same side of said surface of said patient support as said first x-ray radiator, said mount having a mounting element allowing said mount to be attached to a ceiling of a room in which said C-arm examination apparatus is disposed, at a location allowing said radiation receiver to selectively detect X-rays emitted by said first X-ray radiator or X-rays emitted by said second X-ray radiator.

2. An X-ray diagnostic installation as claimed in claim 1 wherein said radiation receiver is mounted on said C-arm of said C-arm examination apparatus allowing said radiation receiver to be rotated so as to be aligned relative to each of said first X-ray radiator and said second X-ray radiator.

3. An X-ray diagnostic installation as claimed in claim 2 wherein said radiation receiver is mounted for rotation around an axis disposed perpendicularly to a plane defined by said C-arm.

4. An X-ray diagnostic installation as claimed in claim 1 wherein a patient on said patient support has a patient axis associated therewith, and wherein said radiation receiver and said second X-ray radiator are movable relative to each other parallel to said patient axis.

5. An X-ray diagnostic installation as claimed in claim 4 wherein said C-arm examination apparatus comprises a guide connected to said C-arm for moving said C-arm parallel to said patient axis.

6. An X-ray diagnostic installation as claimed in claim 4 wherein said mount for said second X-ray radiator comprises a guide connected to said second X-ray radiator for moving said second X-ray radiator parallel to said patient axis.

7. An X-ray diagnostic installation as claimed in claim 1 wherein said radiation receiver is an X-ray image intensifier system.

8. An X-ray diagnostic installation as claimed in claim 1 wherein said radiation receiver is a flat image detector.

9. An X-ray diagnostic installation as claimed in claim 8 wherein said flat image detector is a solid-state matrix detector system.

10. An X-ray diagnostic installation as claimed in claim 9 wherein said solid-state matrix detector system is an a-Si detector.

11. An X-ray diagnostic installation as claimed in claim 1 wherein said mount for said second X-ray radiator comprises a vertically telescoping element having a free end to which said second X-ray radiator is attached.

12. An X-ray diagnostic installation as claimed in claim 1 wherein a patient on said patient support has a patient axis associated therewith, and wherein said mount for said second X-ray radiator allows rotation of said second X-ray radiator around a horizontal rotational axis proceeding perpendicularly to said patient axis.

13. An X-ray diagnostic installation as claimed in claim 1 wherein said mount or said second X-ray radiator allows said second X-ray radiator to be rotated to a position wherein an X-ray bundle emitted by said second X-ray radiator proceeds in a horizontal direction, and wherein said C-arm examination apparatus allows rotation of said radiation receiver toward said second X-ray radiator so that said X-ray bundle is incident on said radiation receiver.

* * * * *